(12) United States Patent
Wahlstrand

(10) Patent No.: US 10,084,250 B2
(45) Date of Patent: Sep. 25, 2018

(54) EXTENSIBLE IMPLANTABLE MEDICAL LEAD

(75) Inventor: Carl D. Wahlstrand, Lino Lakes, MN (US)

(73) Assignee: MEDTRONIC, INC., Minneapolis, MN (US)

(*) Notice: Subject to any disclaimer, the term of this patent is extended or adjusted under 35 U.S.C. 154(b) by 253 days.

(21) Appl. No.: 13/598,911

(22) Filed: Aug. 30, 2012

(65) Prior Publication Data

US 2012/0330383 A1    Dec. 27, 2012

Related U.S. Application Data

(62) Division of application No. 11/346,486, filed on Feb. 1, 2006, now Pat. No. 8,280,526.

(60) Provisional application No. 60/649,237, filed on Feb. 1, 2005.

(51) Int. Cl.
*A61N 1/05*     (2006.01)
*H01R 11/18*   (2006.01)
*H01R 4/36*    (2006.01)

(52) U.S. Cl.
CPC ........... *H01R 11/18* (2013.01); *A61N 1/0534* (2013.01); *A61N 1/0551* (2013.01); *H01R 4/36* (2013.01); *H01R 2201/12* (2013.01)

(58) Field of Classification Search
CPC ............ A61N 1/0488; A61N 2001/086; A61B 18/1492; A61B 2018/00107; H01B 1/1083; A61M 25/0045; A61M 25/005; C08L 27/18
USPC .................................. 607/2–9, 115–119, 122
See application file for complete search history.

(56) References Cited

U.S. PATENT DOCUMENTS

| | | | | |
|---|---|---|---|---|
| 4,033,355 A * | 7/1977 | Amundson | ................ | 607/122 |
| 5,308,664 A * | 5/1994 | House et al. | ................ | 428/34.9 |
| 5,466,252 A * | 11/1995 | Soukup et al. | ............... | 607/116 |
| 5,609,622 A * | 3/1997 | Soukup et al. | ............... | 607/122 |
| 6,920,361 B2 * | 7/2005 | Williams | ................ | 607/122 |
| 2002/0111663 A1* | 8/2002 | Dahl et al. | ................ | 607/122 |
| 2004/0024442 A1* | 2/2004 | Sowinski et al. | ........... | 623/1.13 |
| 2005/0065587 A1* | 3/2005 | Gryzwa | ................ | 607/122 |
| 2005/0080471 A1* | 4/2005 | Chitre et al. | ................ | 607/122 |
| 2010/0256528 A1 | 10/2010 | Lippert et al. | | |
| 2010/0256604 A1 | 10/2010 | Lippert et al. | | |
| 2010/0268310 A1 | 10/2010 | Bonde et al. | | |
| 2010/0331938 A1 | 12/2010 | Sommer | | |

(Continued)

FOREIGN PATENT DOCUMENTS

| | | |
|---|---|---|
| EP | 0617978 | 10/1994 |
| EP | 0624383 | 11/1994 |

(Continued)

OTHER PUBLICATIONS

PCT/US2004/042081: Search Report and Written Opinion.

(Continued)

*Primary Examiner* — Allen Porter, Jr.
(74) *Attorney, Agent, or Firm* — Withers & Keys, LLC

(57) ABSTRACT

An extensible medical lead comprises at least one proximal contact, at least one distal electrode, and having at least one conductive filer electrically coupled between the proximal contacts and the distal stimulation electrode. The lead further comprises an outer jacket made of a longitudinally compressible material. The conductive filer may also be coiled to provide extensibility.

6 Claims, 14 Drawing Sheets

(56) References Cited

U.S. PATENT DOCUMENTS

| | | |
|---|---|---|
| 2011/0015713 A1 | 1/2011 | Min |
| 2011/0034983 A1 | 2/2011 | Min |
| 2011/0071599 A1 | 3/2011 | Olsen |
| 2011/0071604 A1 | 3/2011 | Wahlstrand |
| 2011/0071605 A1 | 3/2011 | Wahlstrand |
| 2011/0112615 A1 | 5/2011 | Hoegh et al. |
| 2011/0230943 A1 | 9/2011 | Johnson et al. |
| 2011/0251487 A1 | 10/2011 | Magnin et al. |
| 2011/0319905 A1 | 12/2011 | Palme et al. |
| 2012/0010689 A1 | 1/2012 | Wahlstrand |
| 2012/0035616 A1 | 2/2012 | Olsen et al. |
| 2012/0035694 A1 | 2/2012 | Olsen |
| 2012/0035695 A1 | 2/2012 | Olsen et al. |
| 2012/0035696 A1 | 2/2012 | Kern |
| 2012/0035697 A1 | 2/2012 | Stone |
| 2012/0035951 A1 | 2/2012 | Goetz |
| 2012/0041528 A1 | 2/2012 | Mehdizadeh et al. |
| 2012/0041529 A1 | 2/2012 | Olsen |
| 2012/0046722 A1 | 2/2012 | Olsen |
| 2012/0053664 A1 | 3/2012 | Hegland |
| 2012/0059467 A1 | 3/2012 | Drew |
| 2012/0130461 A1 | 5/2012 | Olsen |
| 2012/0330383 A1 | 12/2012 | Wahlstrand |
| 2013/0296991 A1 | 11/2013 | Alexander et al. |
| 2014/0107746 A1 | 4/2014 | Alexander et al. |
| 2014/0200643 A1 | 7/2014 | Wahlstrand |
| 2014/0288626 A1 | 9/2014 | Alexander et al. |
| 2014/0345132 A1 | 11/2014 | Mehdizadeh et al. |
| 2014/0350654 A1 | 11/2014 | Olsen et al. |
| 2015/0082618 A1 | 3/2015 | Hegland |
| 2015/0170792 A1 | 6/2015 | Alford |

FOREIGN PATENT DOCUMENTS

| | | |
|---|---|---|
| EP | 0713714 | 5/1996 |
| EP | 0760196 | 3/1997 |
| EP | 0920239 | 6/1999 |
| EP | 1273922 | 1/2003 |
| EP | 1424095 | 6/2004 |
| EP | 1466576 | 10/2004 |
| EP | 1625875 | 2/2006 |
| EP | 1632265 | 3/2006 |
| EP | 1935449 | 6/2008 |
| GB | 2429154 | 2/2007 |
| JP | 07/255863 | 10/1995 |
| JP | 11/086641 | 3/1999 |
| WO | WO95/032673 | 12/1995 |
| WO | WO96/016694 | 6/1996 |
| WO | WO96/028951 | 9/1996 |
| WO | WO97/041923 | 11/1997 |
| WO | WO98/048896 | 11/1998 |
| WO | WO99/010035 | 3/1999 |
| WO | WO99/019020 | 4/1999 |
| WO | WO99/060370 | 11/1999 |
| WO | WO00/027279 | 5/2000 |
| WO | WO01/080940 | 11/2001 |
| WO | WO02/000292 | 1/2002 |
| WO | WO02/083236 | 10/2002 |
| WO | WO03/037429 | 5/2003 |
| WO | WO03/061755 | 7/2003 |
| WO | WO03/063946 | 8/2003 |
| WO | WO03/063948 | 8/2003 |
| WO | WO03/063952 | 8/2003 |
| WO | WO03/063953 | 8/2003 |
| WO | WO03/063954 | 8/2003 |
| WO | WO03/063955 | 8/2003 |
| WO | WO03/063956 | 8/2003 |
| WO | WO03/063957 | 8/2003 |
| WO | WO03/075797 | 9/2003 |
| WO | WO03/092326 | 11/2003 |
| WO | WO03/095022 | 11/2003 |
| WO | WO04/012809 | 2/2004 |
| WO | WO04/052448 | 6/2004 |
| WO | WO04/073040 | 8/2004 |
| WO | WO05/030322 | 4/2005 |
| WO | WO05/032654 | 4/2005 |
| WO | WO05/102444 | 11/2005 |
| WO | WO05/102445 | 11/2005 |
| WO | WO05/102446 | 11/2005 |
| WO | WO05/102447 | 11/2005 |
| WO | WO06/031317 | 3/2006 |
| WO | WO06/093685 | 9/2006 |
| WO | WO06/093686 | 9/2006 |
| WO | WO06/118640 | 11/2006 |
| WO | WO06/118641 | 11/2006 |
| WO | WO07/047966 | 4/2007 |
| WO | WO07/124273 | 11/2007 |
| WO | WO07/126657 | 11/2007 |
| WO | WO07/149757 | 12/2007 |
| WO | WO08/088568 | 7/2008 |
| WO | WO08/100839 | 8/2008 |
| WO | WO08/100840 | 8/2008 |
| WO | WO08/111986 | 9/2008 |
| WO | WO08/130409 | 10/2008 |
| WO | WO08/134196 | 11/2008 |
| WO | WO08/140376 | 11/2008 |
| WO | WO09/011440 | 9/2009 |
| WO | WO09/134901 | 11/2009 |
| WO | WO10/062988 | 6/2010 |
| WO | WO10/126871 | 11/2010 |
| WO | WO10/126877 | 11/2010 |
| WO | WO10/126884 | 11/2010 |
| WO | WO10/126887 | 11/2010 |
| WO | WO10/126935 | 11/2010 |
| WO | WO10/126939 | 11/2010 |
| WO | WO10/126943 | 11/2010 |
| WO | WO10/126946 | 11/2010 |
| WO | WO10/126949 | 11/2010 |
| WO | WO10/126975 | 11/2010 |
| WO | WO10/135440 | 11/2010 |
| WO | WO11/019416 | 2/2011 |
| WO | WO12/103419 | 8/2012 |
| WO | WO13/158189 | 10/2013 |

OTHER PUBLICATIONS

PCT/US2005/000322: Search Report and Written Opinion.
PCT/US2008/053540: Search Report and Written Opinion.
PCT/US2008/053541: Search Report and Written Opinion.
PCT/US2008/059358: Search Report and Written Opinion.
PCT/US2009/036461: Search Report and Written Opinion.
PCT/US2010/032516: Search Report and Written Opinion.
PCT/US2010/032526: Search Report and Written Opinion.
PCT/US2010/032543: Search Report and Written Opinion.
PCT/US2010/032560: Search Report and Written Opinion.
PCT/US2010/032567: Search Report and Written Opinion.
PCT/US2010/032666: Search Report and Written Opinion.
PCT/US2010/032671: Search Report and Written Opinion.
PCT/US2010/032675: Search Report and Written Opinion.
PCT/US2010/032682: Search Report and Written Opinion.
PCT/US2010/032719: Search Report and Written Opinion.
PCT/US2013/023637: Search Report and Written Opinion.
Baker et al., "Evaluation of Specific Absorption Rates as a Dosimeter of MRI-Related Implant Heating", Journal of Magnetic Resonance Imaging 20:315-320 (2004).
Baker, K., et al., "Neurostimulation Systems: Assessment of Magnetic Field Interactions Associated with 1.5 and 3-Tesla MR Systems", J. Magn. Reson. Imaging, Jan. 2005, 21(1);72-7.
Chung, D.D.L., "Carbon Fiber Composites", 1994, chapter 1, p. 8, table 1.2, Elsevier, ISBN: 978-0-7506-9169-7.
Chung, D.D.L., Comparison of Submicron-Diameter Carbon Filaments and Conventional Carbon Fibers as Fillers in Composite Materials, Carbon 39 (2001) pp. 1119-1125, Elsevier Science Ltd.
Chung, D.D.L., Electromagnetic Interference Shielding Effectiveness of Carbon Materials, Carbon 29 (2001) pp. 279-285, Elsevier Science Ltd.
Engdahl, Tomi, "Ground Loop Basics." Web Jan. 4, 2009, ePanorama. net www.epanorama.net/documents/groundloop/basics.html U.S. Appl. No. 11/739,787.

(56) References Cited

OTHER PUBLICATIONS

Finelli, D., et al., "MRI Imaging-Related Heating of Deep Brain Stimulation Electrodes: In Vitro Study", AJNR AM. J. Neuroadiol 23:1, Nov./Dec. 2002.

Jou, W.S. "A Novel Structure of Woven Continuous-Carbon Fiber Composites with High Electromagnetic Shielding", Journal of Electronic Materials, vol. 33, No. 3, Mar. 1, 2004, pp. 162-170(9), Minerals, Metals and Materials Society, http://findarticles.com/p/articles/mi_qu3776/is_200403/ai_n9405_582/print.

Kolin, et al., "An Electromagnetic Catheter Flow Meter for Determination of Blood Flow in Major Arteries," Department of Biophysics, Physiology, and Radiology, University of California School of Medicine (Los Angeles) Jan. 19, 1988, Proc. N.A.S. vol. 59, pp. 808-815.

Kolin, et al., "An Electromagnetic Intravascular Blood-Flow Sensor", Department of Biophysics, University of California School of Medicine (Los Angeles), Mar. 20, 1967, Proc. N.A.S., vol. 57, pp. 1331-1337.

Kolin, et al., "Miniaturization of the Electromagnetic Blood Flow Meter and Its Use for the Recording of Circulatory Responses of Conscious Animals to Sensory Stimuli", Department of Biophysics, University of California at Los Angeles, Aug. 1959, Proc. N.A.S. vol. 45(8), pp. 1312-1321.

Medtronic Activa Product Family and Procedure Solution Brochure, Medtronic, Inc, 2001.

Medtronic Neurostimulation Systems Brochure, Medtronic, Inc., 2002.

Quick et al., "Endourethral MRI", Magnetic Resonance in Medicine, 45:138-146, 2001.

Rezai, A., et al., "Neurostimulation System Used for Deep Brain Stimulation (DBS): MR Safety Issues and Implications of Failing to Follow Safety Recommendations" Investigative Radiology, May 2004, vol. 39, Issue 5, pp. 300-303.

Rezai, A., et al., "Neurostimulation Systems for Deep Brain Stimulation In Vitro Evaluation of Magnetic Resonance Imaging-Related Healing at 1.5 Tesla", Journal of Magnetic Reson. Imaging 2002; 15:241-50.

* cited by examiner

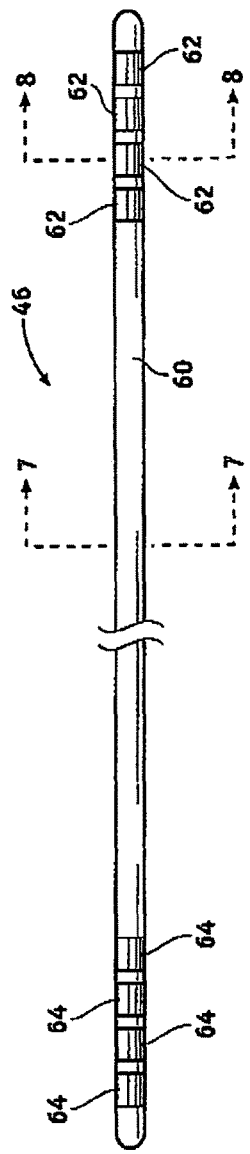
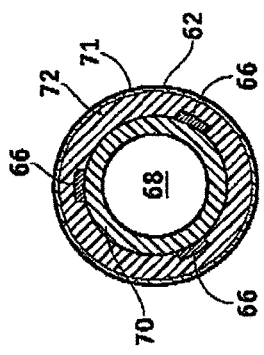
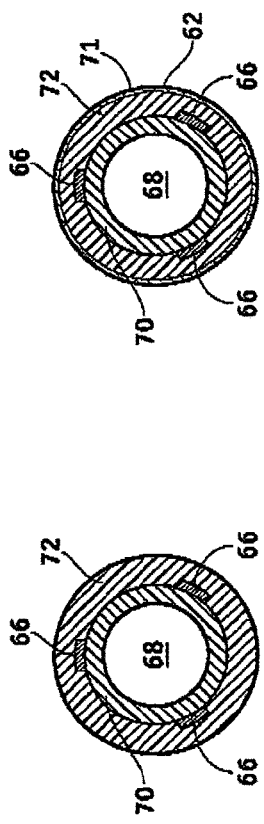
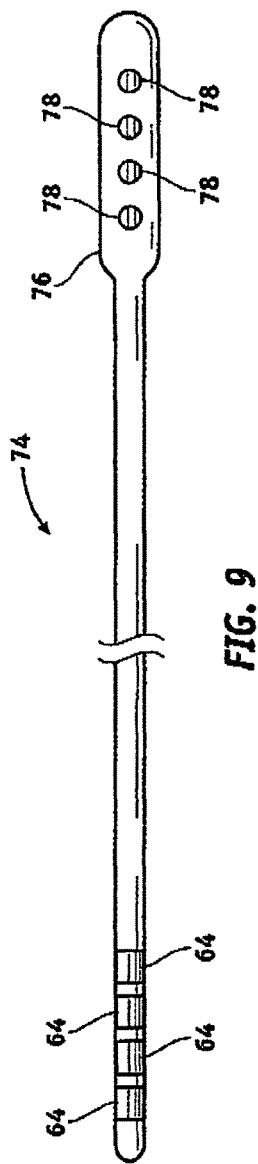

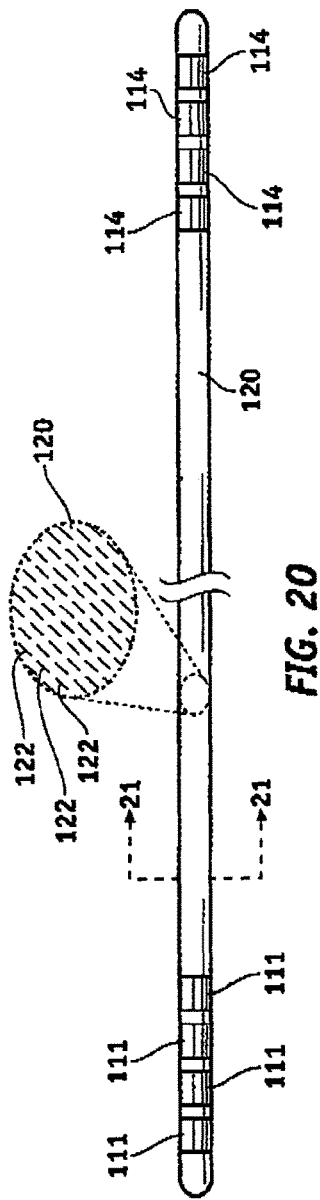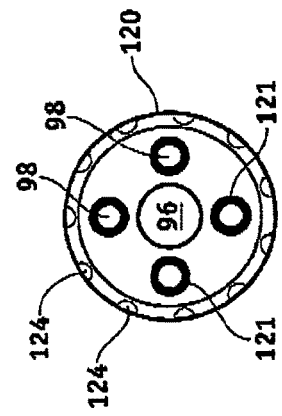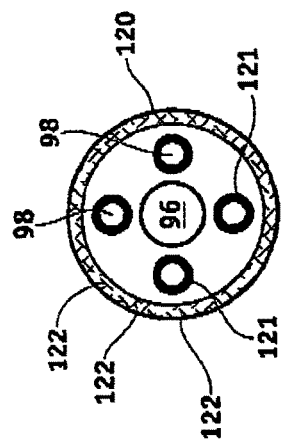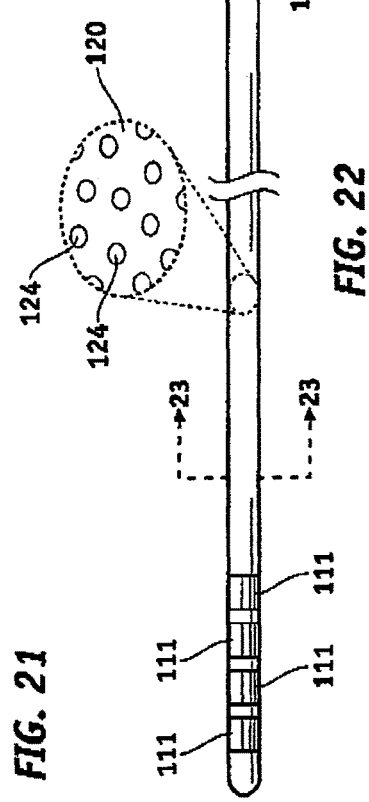

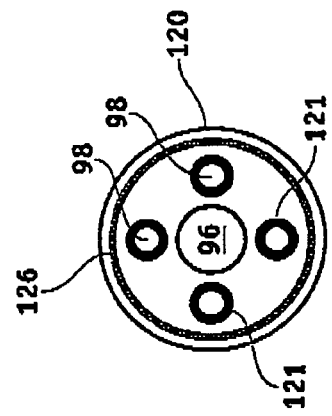
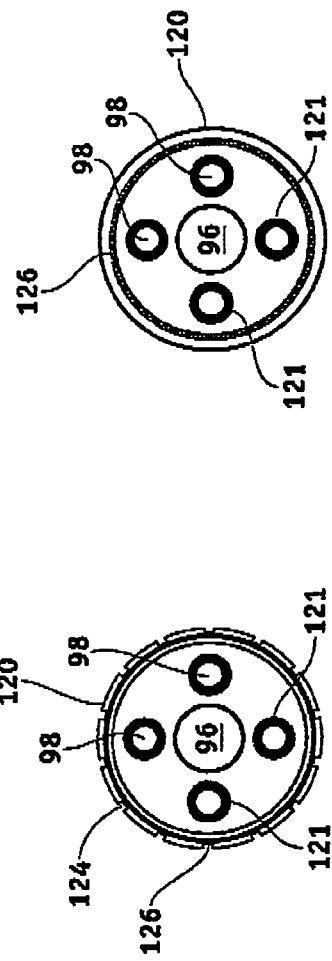
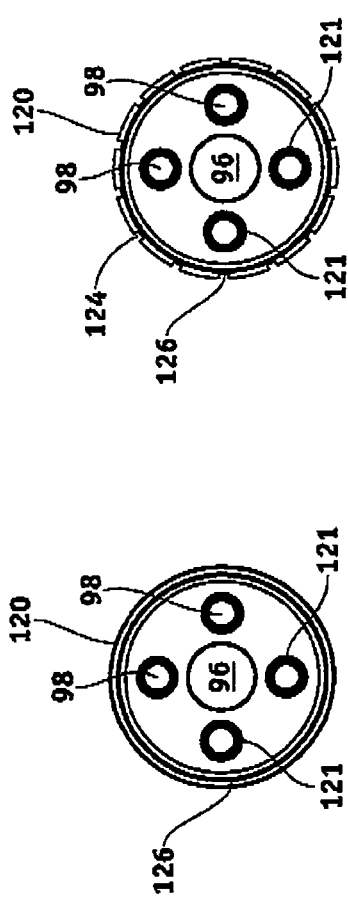
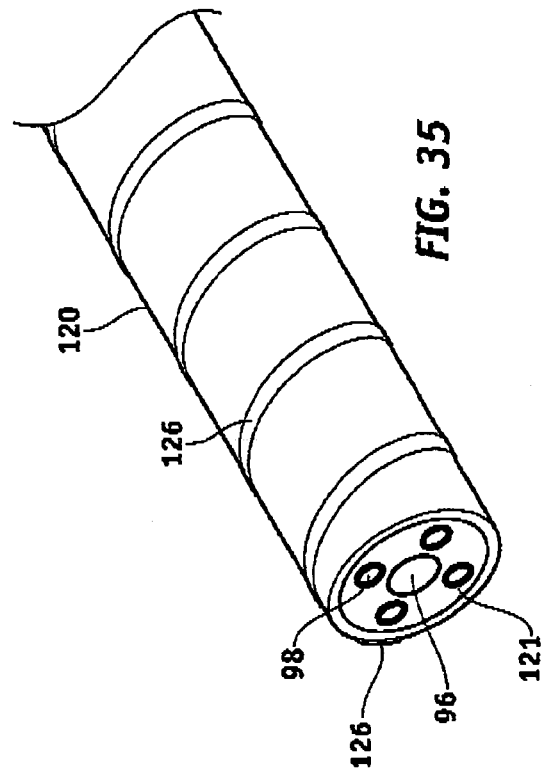
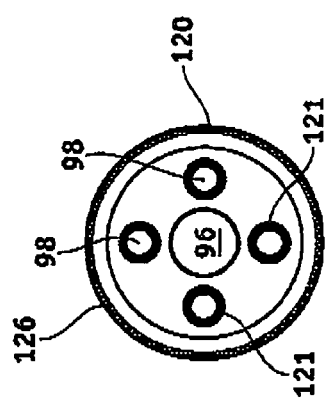

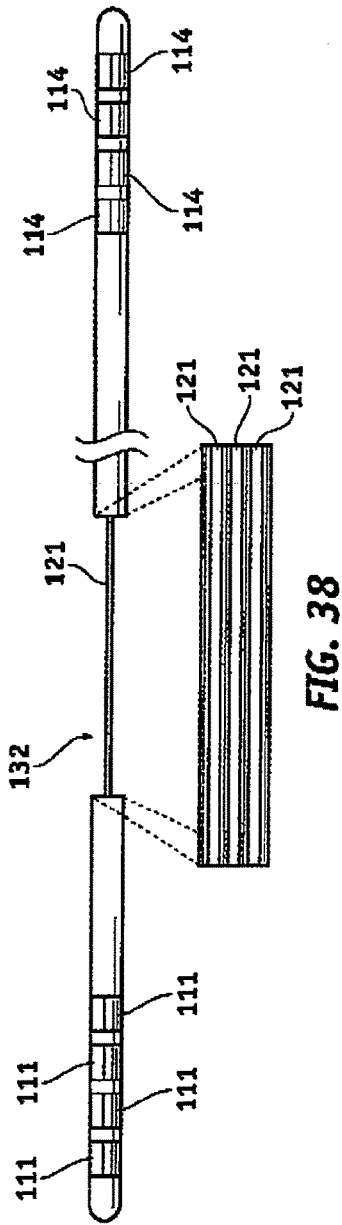
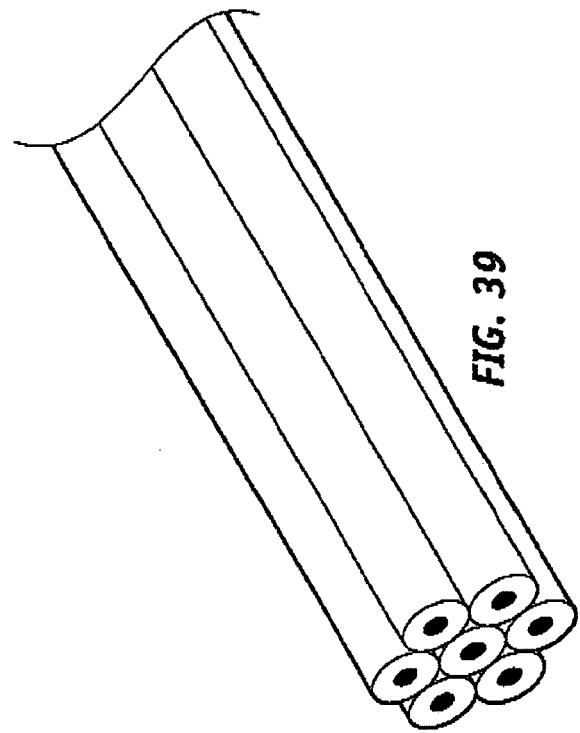
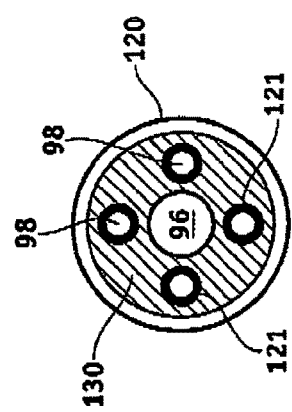

EXTENSIBLE IMPLANTABLE MEDICAL LEAD

CROSS-REFERENCES TO RELATED APPLICATIONS

This application is a divisional of U.S. application Ser. No. 11/346,486, filed on Feb. 1, 2006 now U.S. Pat. No. 8,280,526, which is entitled Extensible Implantable Medical Lead and which claims the benefit of U.S. Provisional Application No. 60/649,237 filed Feb. 1, 2005, both of which are incorporated herein by reference.

FIELD OF THE INVENTION

The present invention generally relates to implantable medical devices (IMDs), and more particularly to implantable medical leads.

BACKGROUND OF THE INVENTION

Implantable medical devices are commonly used today to treat patients suffering from various ailments. Such implantable devices may be utilized to treat conditions such as pain, incontinence, sleep disorders, and movement disorders such as Parkinson's disease and epilepsy. Such therapies also appear promising in the treatment of a variety of psychological, emotional, and other physiological conditions.

One known type of implantable medical device, a neurostimulator, delivers mild electrical impulses to neural tissue using an electrical lead. For example, to treat pain, electrical impulses may be directed to specific sites. Such neurostimulation may result in effective pain relief and a reduction in the use of pain medications and/or repeat surgeries.

Typically, such devices are totally implantable and may be controlled by a physician or a patient through the use of an external programmer. Current systems generally include a non-rechargeable primary cell neurostimulator, a lead extension, and a stimulation lead, and the two main classes of systems may be referred to as: (1) Spinal Cord Stimulation (SCS) and (2) Deep Brain Stimulation (DBS).

An SCS stimulator may be implanted in the abdomen, upper buttock, or pectoral region of a patient and may include at least one extension running from the neurostimulator to the lead or leads which are placed somewhere along the spinal cord. Each of the leads (to be discussed in detail hereinbelow) currently contains from one to eight electrodes. Each extension (likewise to be discussed in detail below) is plugged into or connected to the neurostimulator at a proximal end thereof and is coupled to and interfaces with the lead or leads at a distal end of the extension or extensions.

The implanted neuro stimulation system is configured to send mild electrical pulses to the spinal cord. These electrical pulses are delivered through the lead or leads to regions near the spinal cord or the nerve selected for stimulation. Each lead includes a small insulated wire coupled to an electrode at the distal end thereof through which the electrical stimulation is delivered. Typically, the lead also comprises a corresponding number of internal wires to provide separate electrical connection to each electrode such that each electrode may be selectively used to provide stimulation. Connection of the lead to an extension may be accomplished by means of a connector block including, for example, a series or combination of set-screws, ball-seals, etc. The leads are inserted into metal set screw blocks, and metal set screws are manipulated to press the contacts against the blocks to clamp them in place and provide an electrical connection between the lead wires and the blocks. Such an arrangement is shown in U.S. Pat. No. 5,458,629 issued Oct. 17, 1995 and entitled "Implantable Lead Ring Electrode and Method of Making".

A DBS system comprises similar components (i.e. a neurostimulator, at least one extension, and at least one stimulation lead) and may be utilized to provide a variety of different types of electrical stimulation to reduce the occurrence or effects of Parkinson's disease, epileptic seizures, or other undesirable neurological events. In this case, the neurostimulator may be implanted into the pectoral region of the patient. The extension or extensions may extend up through the patient's neck, and the leads/electrodes are implanted in the brain. The leads may interface with the extension just above the ear on both sides of the patient. The distal end of the lead may contain from four to eight electrodes and, as was the case previously, the proximal end of the lead may connect to the distal end of the extension and held in place by set screws. The proximal portion of the extension plugs into the connector block of the neurostimulator.

Magnetic resonance imaging (MRI) is a relatively new and efficient technique that may be used in the diagnosis of many neurological disorders. It is an anatomical imaging tool which utilizes non-ionizing radiation (i.e. no x-rays or gamma rays) and provides a non-invasive method for the examination of internal structure and function. For example, MRI permits the study of the overall function of the heart in three dimensions significantly better than any other imaging method. Furthermore, imaging with tagging permits the non-invasive study of regional ventricular function.

MRI scanning is widely used in the diagnosis of diseases and injuries to the head. In fact, the MRI is now considered by many to be the preferred standard of care, and failure to prescribe MRI scanning can be considered questionable. For example, approximately sixteen million MRIs were performed in 1996 followed by approximately twenty million in the year 2000. It is projected that forty million MRIs will be performed in 2004.

In an MRI scanner, a magnet creates a strong magnetic field which aligns the protons of hydrogen atoms in the body and then exposes them to radio frequency (RF) energy from a transmitter portion of the scanner. This spins the various protons, and they produce a faint signal that is detected by a receiver portion of the scanner. A computer renders these signals into an image. During this process, three electromagnetic fields are produced; i.e. (1) a static magnetic field, (2) a gradient magnetic field, and (3) a radio frequency (RF) field. The main or static magnetic field may typically vary between 0.2 and 3.0 Tesla. A nominal value of 1.5 Tesla is approximately equal to 15,000 Gauss which is 30,000 times greater than the Earth's magnetic field of approximately 0.5 Gauss. The time varying or gradient magnetic field may have a maximum strength of approximately 40 milli-Tesla/meter at a frequency of 0-5 KHz. The RF may, for example, produce thousands of watts at frequencies of between 8-128 MHz. For example, up to 20,000 watts may be produced at 64 MHz and a static magnetic field of 1.5 Tesla; that is, 20 times more power than a typical toaster. Thus, questions have arisen regarding the potential risk associated with undesirable interaction between the MRI environment and the above-described neurostimulation systems; e.g. forces and torque on the implantable device within the MRI scanner caused by the static magnetic field, RF-induced heating, induced currents due to gradient magnetic fields, device damage, and image distortion.

Additionally, as a patient implanted with an IMD moves, some regions of the body expand and/or contract exerting loading forces on the implanted leads that may cause lead failure, axial migration of the electrodes, and/or body tissue stress, possibly causing the patient to experience pain.

Accordingly, it would be desirable to provide an implantable medical device that may be safely operated in an MRI environment. It would be further desirable to provide an implantable medical lead that is extendable to accommodate changes in length resulting from patient movement. Other desirable features and characteristics of the present invention will become apparent from the subsequent detailed description of the invention and the appended claims, taken in conjunction with the accompanying drawings and this background of the invention.

BRIEF SUMMARY OF THE INVENTION

According to an aspect of the invention, there is provided an extensible medical lead having at least one proximal contact, at least one distal electrode, and having at least one conductive filer electrically coupled between the proximal contacts and the distal stimulation electrode. A outer jacket is made of a longitudinally compressible material.

BRIEF DESCRIPTION OF THE DRAWINGS

The present invention will hereinafter be described in conjunction with the accompanying drawing, wherein like reference numerals denote like elements.

FIG. 6 is a top view of the lead shown in FIG. 2;

FIGS. 7 and 8 are cross-sectional views taken along lines 7-7 and 8-8, respectively, in FIG. 6;

FIG. 9 is a top view of an alternate lead configuration;

FIGS. 20 and 21 are longitudinal and cross-sectional views, respectively, of a first embodiment of the inventive lead;

FIGS. 22 and 23 are longitudinal and cross-sectional views, respectively, of a further embodiment of the present invention;

FIGS. 31-34 are isometric and cross-sectional views illustrating a still further embodiment of the present invention;

FIGS. 35 and 36 are isometric and cross-sectional views, respectively, of yet another embodiment of the present invention;

FIGS. 37 and 38 illustrate still further embodiments of the present invention;

FIG. 39 is an isometric view of yet another embodiment of the present invention;

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

Figure 1:
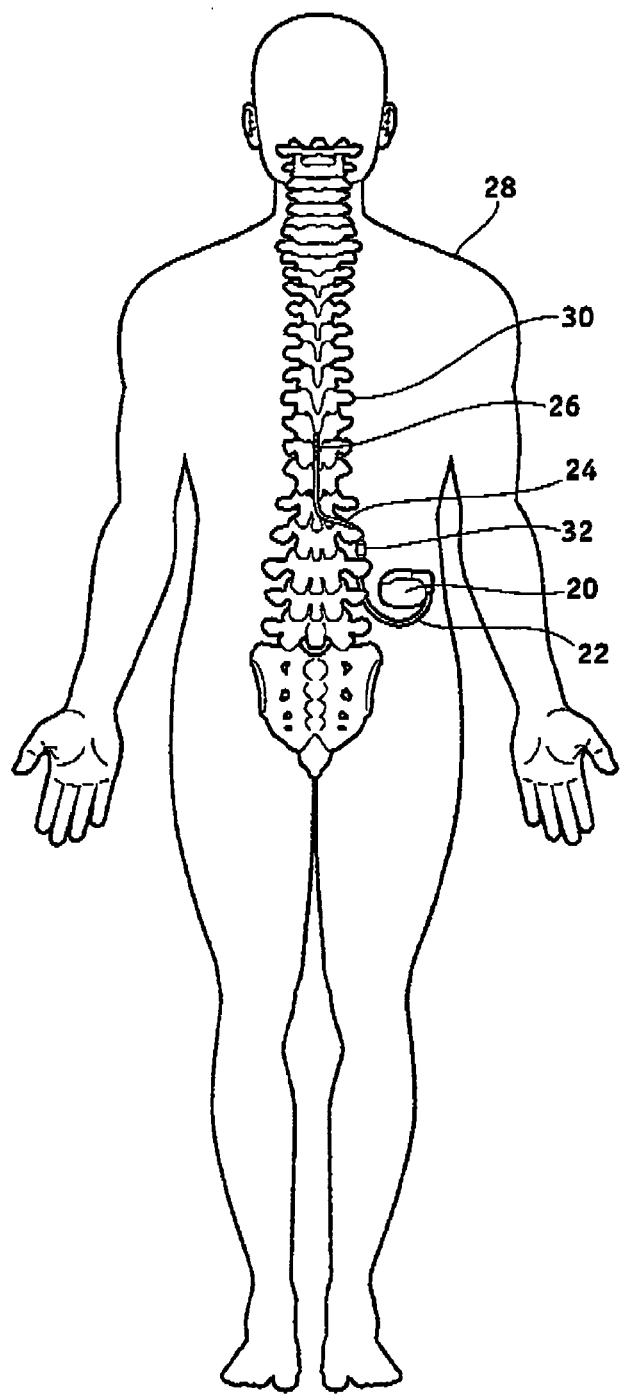
FIG. 1 illustrates a typical spinal cord stimulation system implanted in a patient.

FIG. 1 illustrates a typical SCS system implanted in a patient. As can be seen, the system comprises a pulse generator such as a SCS neurostimulator 20, a lead extension 22 having a proximal end coupled to neurostimulator 20 as will be more fully described below, and a lead 24 having a proximal end coupled to the distal end of extension 22 and having a distal end coupled to one or more electrodes 26. Neurostimulator 20 is typically placed in the abdomen of a patient 28, and lead 24 is placed somewhere along spinal cord 30. As stated previously, neurostimulator 20 may have one or two leads each having four to eight electrodes. Such a system may also include a physician programmer and a patient programmer (not shown). Neurostimulator 20 may be considered to be an implantable pulse generator of the type available from Medtronic, Inc. and capable of generating multiple pulses occurring either simultaneously or one pulse shifting in time with respect to the other, and having independently varying amplitudes and pulse widths. Neurostimulator 20 contains a power source and the electronics for sending precise, electrical pulses to the spinal cord to provide the desired treatment therapy. While neurostimulator 20 typically provides electrical stimulation by way of pulses, other forms of stimulation may be used such as continuous electrical stimulation.

Lead 24 is a small medical wire having special insulation thereon and includes one or more insulated electrical conductors each coupled at their proximal end to a connector and to contacts/electrodes 26 at its distal end. Some leads are designed to be inserted into a patient percutaneously (e.g. the Model 3487A Pisces—Quad® lead available from Medtronic, Inc.), and some are designed to be surgically implanted (e.g. Model 3998 Specify® lead, also available from Medtronic, Inc.). Lead 24 may contain a paddle at its distant end for housing electrodes 26; e.g. a Medtronic paddle having model number 3587A. Alternatively, electrodes 26 may comprise one or more ring contacts at the distal end of lead 24 as will be more fully described below.

While lead 24 is shown as being implanted in position to stimulate a specific site in spinal cord 30, it could also be positioned along the peripheral nerve or adjacent neural tissue ganglia or may be positioned to stimulate muscle tissue. Furthermore, electrodes/contacts 26 may be epidural, intrathecal or placed into spinal cord 30 itself. Effective spinal cord stimulation may be achieved by any of these lead placements. While the lead connector at proximal end of lead 24 may be coupled directly to neurostimulator 20, the lead connector is typically coupled to lead extension 22 as is shown in FIG. 1. An example of a lead extension is Model 7495 available from Medtronic, Inc.

A physician's programmer (not shown) utilizes telemetry to communicate with the implanted neurostimulator 20 to enable the physician to program and manage a patient's therapy and troubleshoot the system. A typical physician's programmer is available from Medtronic, Inc. and bears Model No. 7432. Similarly, a patient's programmer (also not shown) also uses telemetry to communicate with neurostimulator 20 so as to enable the patient to manage some aspects of their own therapy as defined by the physician. An example of a patient programmer is Model 7434 Itrel® 3 EZ Patient Programmer available from Medtronic, Inc.

Implantation of a neurostimulator typically begins with the implantation of at least one stimulation lead while the patient is under a local anesthetic. While there are many spinal cord lead designs utilized with a number of different implantation techniques, the largest distinction between leads revolves around how they are implanted. For example, surgical leads have been shown to be highly effective, but require a laminectomy for implantation. Percutaneous leads can be introduced through a needle, a much easier procedure. To simplify the following explanation, discussion will focus on percutaneous lead designs, although it will be understood by those skilled in the art that the inventive aspects are equally applicable to surgical leads. After the lead is implanted and positioned, the lead's distal end is typically anchored to minimize movement of the lead after implantation. The lead's proximal end is typically configured to connect to a lead extension 22. The proximal end of the lead extension is then connected to the neurostimulator 20.

Figure 2:
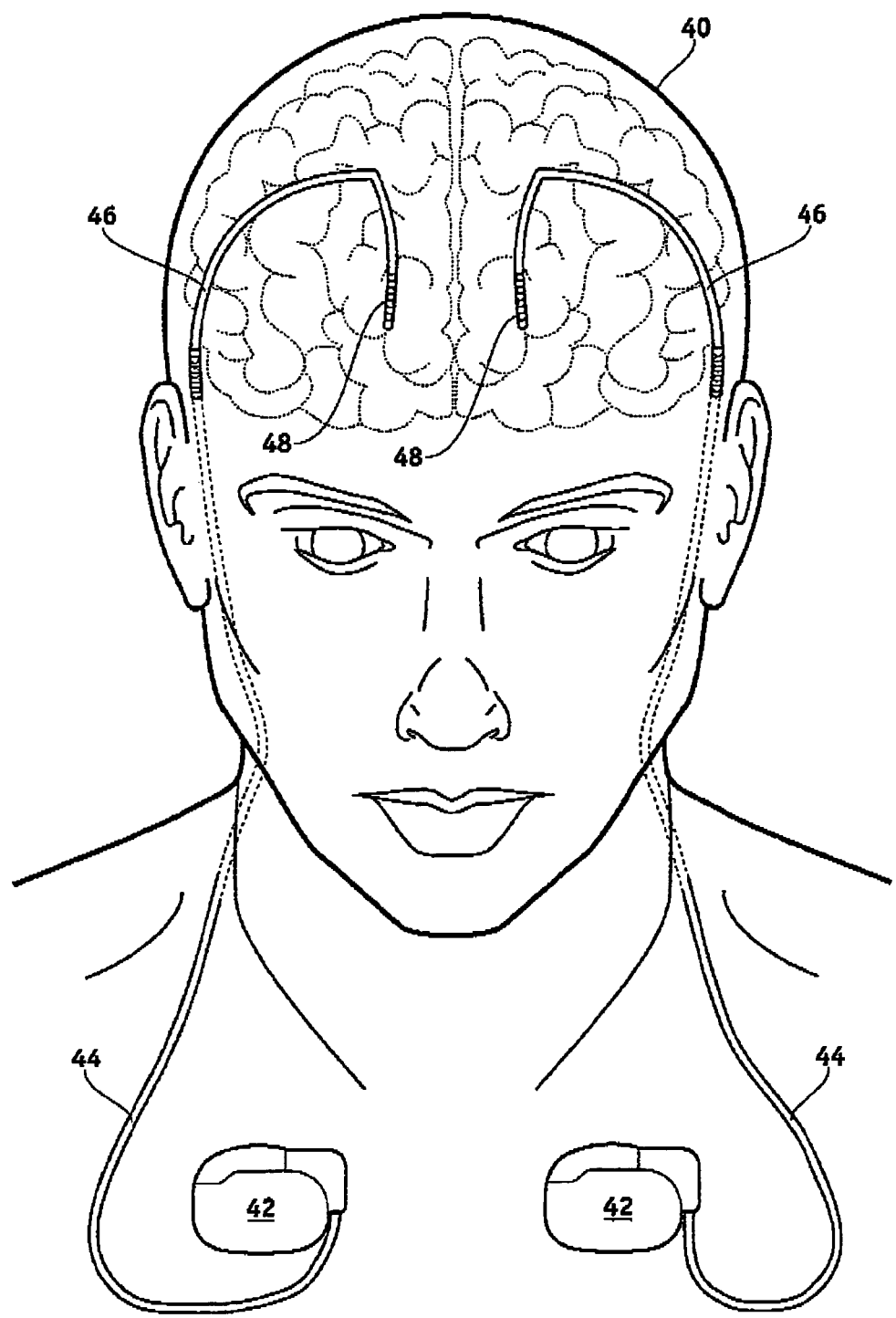
FIG. 2 illustrates a typical deep brain stimulation system implanted in a patient.

FIG. 2 illustrates a DBS system implanted in a patient 40 and comprises substantially the same components as does an SCS; that is, at least one neurostimulator, at least one extension, and at least one stimulation lead containing one or more electrodes. As can be seen, each neurostimulator 42 is implanted in the pectoral region of patient 40. Extensions 44 are deployed up through the patient's neck, and leads 46 are implanted in the patient's brain as is shown at 48. As can be seen, each of leads 46 is connected to its respective extension 44 just above the ear on both sides of patient 40.

Figure 3:
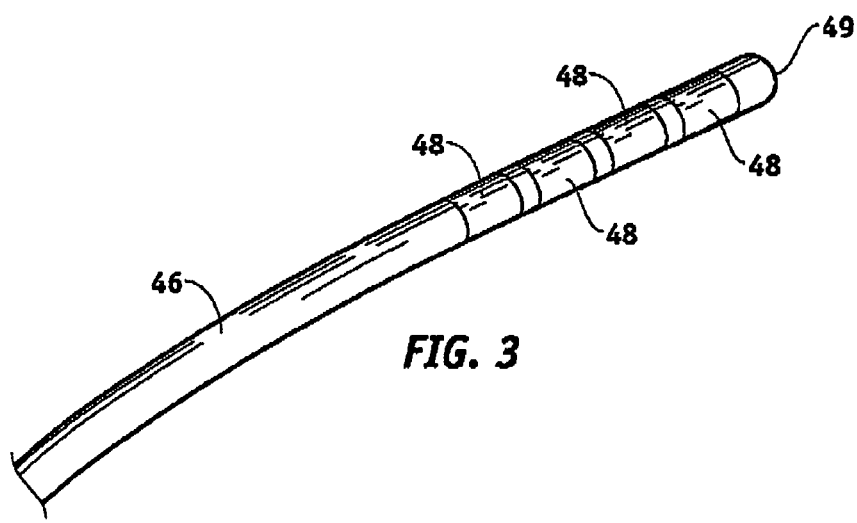
FIG. 3 is an isometric view of the distal end of the lead shown in FIG. 2.

FIG. 3 is an isometric view of the distal end of lead 46. In this case, four ring electrodes 48 are positioned on the distal end of lead 46 and coupled to internal conductors or filers (not shown) contained within lead 46. Again, while four ring electrodes are shown in FIG. 3, it is to be understood that the number of electrodes can vary to suit a particular application.

Figure 5:
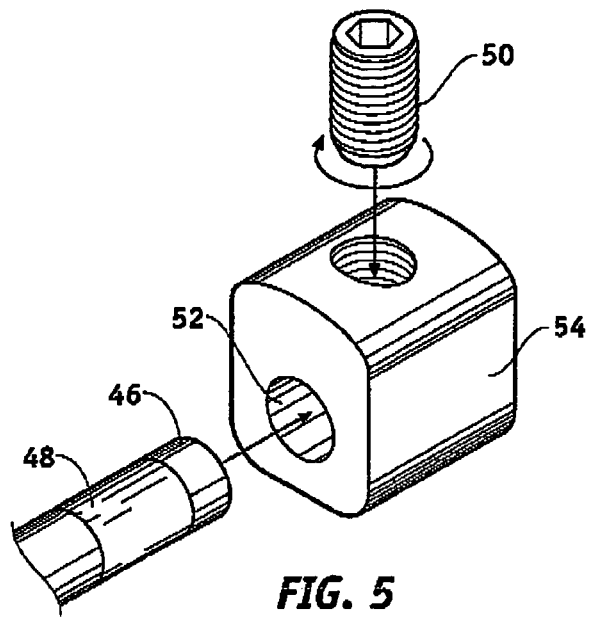
FIG. 5 is an isometric view of an example of a connector screw block suitable for connecting the lead of FIG. 3 to the extension shown in FIG. 4.
Figure 4:
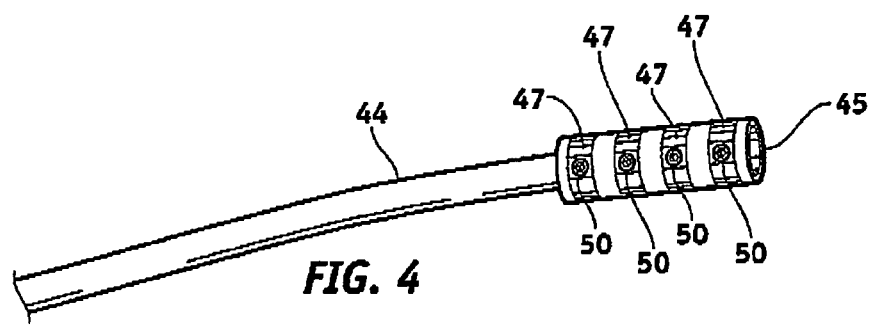
FIG. 4 is an isometric view of the distal end of the extension shown in FIG. 2.

FIG. 4 is an isometric view of the distal end of extension 44, which includes a connector portion 45 having four internal contacts 47. The proximal end of the DBS lead, as shown in FIG. 3, plugs into distal connector 45 of extension 44 and is held in place by means of, for example, a plurality (e.g. four) of set screws 50. For example, referring to FIG. 5, lead 46 terminates in a series of proximal electrical ring contacts 48 (only one of which is shown in FIG. 5). Lead 46 may be inserted through an axially aligned series of openings 52 (again only one shown) in screw block 54. With lead 46 so inserted, a series of set screws 50 (only one shown) are screwed into blocks 54 to drive contacts 48 against blocks 54 and secure and electronically couple lead 46. It should be appreciated, however, that other suitable methods for securing lead 46 to extension 44 may be employed. The proximal portion of extension 44 is secured to neurostimulator 42 as is shown in FIGS. 1 and 2.

FIG. 6 is a top view of lead 46 shown in FIG. 2. FIGS. 7 and 8 are cross-sectional views taken along lines 7-7 and 8-8, respectively, in FIG. 6. Distal end 60 of lead 46 includes at least one electrode 62 (four are shown). As stated previously, up to eight electrodes may be utilized. Each of electrodes 62 is preferably constructed as is shown in FIG. 8. That is, electrode 62 may comprise a conductive ring 71 on the outer surface of the elongate tubing making up distal shaft 60. Each electrode 62 is electrically coupled to a longitudinal wire 66 (shown in FIGS. 7 and 8) which extends to a contact 64 at the proximal end of lead 46. Longitudinal wires 66 may be of a variety of configurations; e.g. discreet wires, printed circuit conductors, etc. From the arrangement shown in FIG. 6, it should be clear that four conductors or filers run through the body of lead 46 to electrically connect the proximal electrodes 64 to the distal electrodes 62. As will be further discussed below, the longitudinal conductors 66 may be spirally configured along the axis of lead 46 until they reach the connector contacts.

The shaft of lead 46 preferably has a lumen 68 extending therethrough for receiving a stylet that adds a measure of rigidity during installation of the lead. The shaft preferably comprises a comparatively stiffer inner tubing member 70 (e.g. a polyamine, polyamide, high density polyethylene, polypropylene, polycarbonate or the like). Polyamide polymers are preferred. The shaft preferably includes a comparatively softer outer tubing member or jacket 72; e.g. silicon or other suitable elastomeric polymer. The conductive rings 71 are preferably of a biocompatible metal such as one selected from the noble group of metals, preferably palladium, platinum or gold and their alloys.

FIG. 9 illustrates an alternative lead 74 wherein distal end 76 is broader (e.g. paddle-shaped) to support a plurality of distal electrodes 78. A lead of this type is shown in FIG. 1. As was the case with the lead shown in FIGS. 6, 7 and 8, distal electrodes 78 are coupled to contacts 64 each respectively by means of an internal conductor or filer. A more detailed description of the leads shown in the FIGS. 6 and 9 may be found in U.S. Pat. No. 6,529,774 issued Mar. 4, 2003 and entitled "Extradural Leads, Neurostimulator Assemblies, and Processes of Using Them for Somatosensory and Brain Stimulation".

Figure 11:
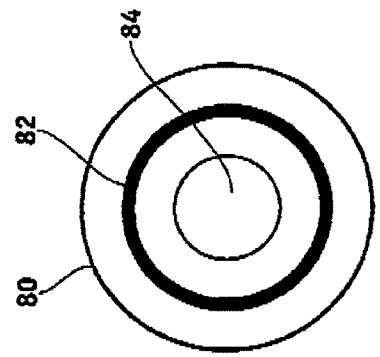
FIGS. 10 and 11 are longitudinal and radial cross-sectional views, respectively, of a helically wound lead of the type shown in FIG. 6.
Figure 10:
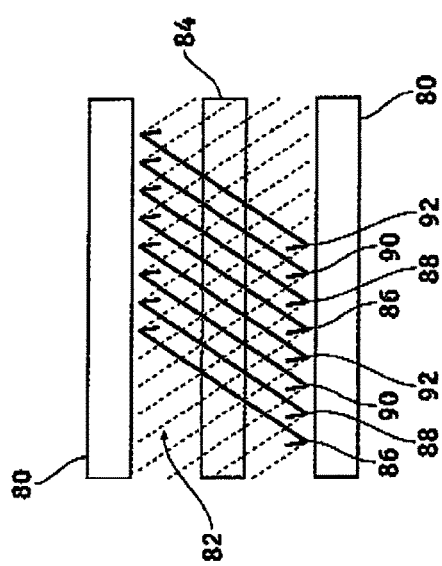

Leads of the type described above may be of the wound helix filer type or of the cabled filer type. FIGS. 10 and 11 are longitudinal and radial cross-sectional views, respectively, of a helically wound lead of the type shown in FIG. 6. The lead comprises an outer lead body or jacket 80; a plurality of helically wound, co-radial lead filers 82; and a stylet lumen 84. As stated previously, a stylet is a stiff, formable insert placed in the lead during implant so as to enable the physician to steer the lead to an appropriate location. FIG. 10 illustrates four separate, co-radially wound filers 86, 88, 90 and 92 which are electrically insulated from each other and electrically couple a single electrode 62 (FIG. 6) to a single contact 64 (FIG. 6).

Figure 13:
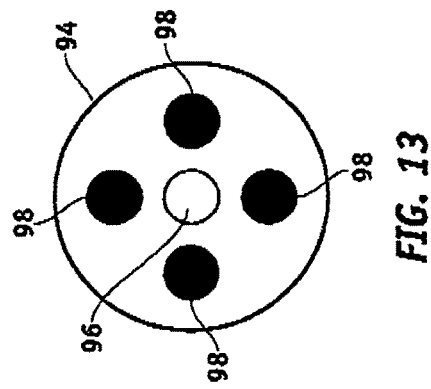
FIGS. 12 and 13 are longitudinal and radial cross-sectional views, respectively, of a cabled lead.
Figure 12:
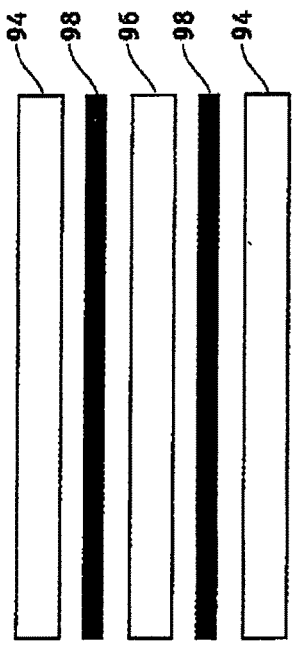

As can be seen, the lead filers 82 have a specific pitch and form a helix of a specific diameter. The helix diameter is relevant in determining the inductance of the lead. These filers themselves also have a specific diameter and are made of a specific material. The filer diameter, material, pitch and helix diameter are relevant in determining the impedance of the lead. In the case of a helically wound lead, the inductance contributes to a frequency dependent impedance. FIGS. 12 and 13 are longitudinal and radially cross-sectional views, respectively, of a cabled lead. The lead comprises outer lead body or jacket 94, stylet lumen 96, and a plurality (e.g. four, eight, etc.) of straight lead filers 98.

Figure 14:
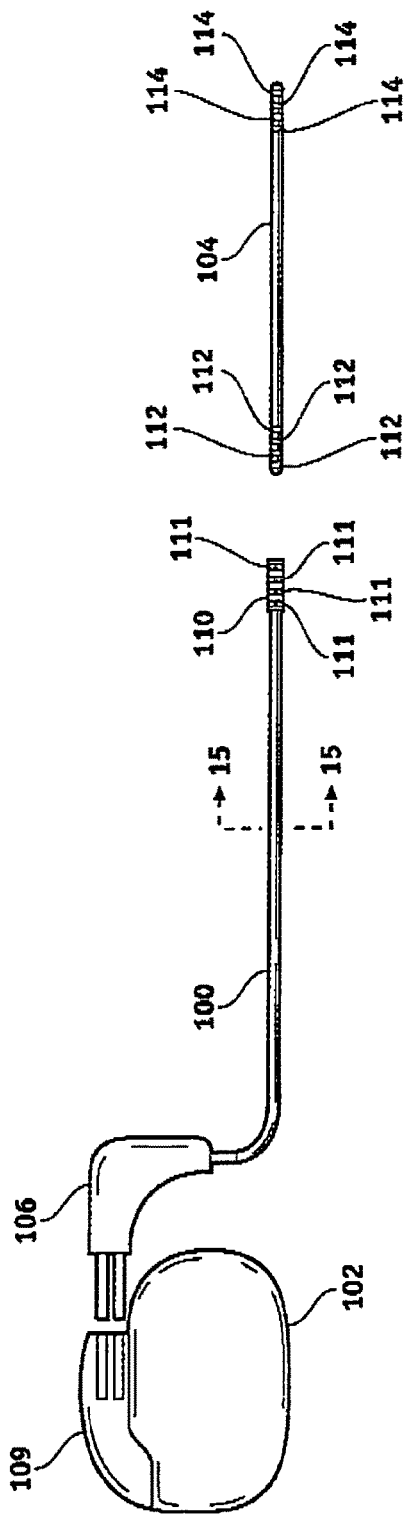
FIG. 14 is an exploded view of a neurostimulation system.

FIG. 14 is an exploded view of a neurostimulation system that includes an extension 100 configured to be coupled between a neurostimulator 102 and lead 104. The proximal portion of extension 100 comprises a connector 106 configured to be received or plugged into connector block 109 of neurostimulator 102. The distal end of extension 100 likewise comprises a connector 110 including internal contacts 111 configured to receive the proximal end of lead 104 having contacts 112 thereon. The distal end of lead 104 includes distal electrodes 114.

Figure 15:
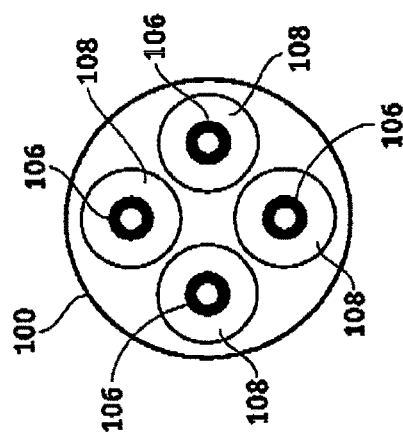
FIG. 15 is a cross-sectional view of the extension shown in FIG. 14 taken along line 15-15.

FIG. 15 is a cross-sectional view of extension 100. Lead extension 100 has a typical diameter of 0.1 inch, which is significantly larger than that of lead 104 so as to make extension 100 more durable than lead 104. Extension 100 differs from lead 104 also in that each filer in lead body 100 is helically wound or coiled in its own lumen 108 and not co-radially wound with the rest of the filers as was the case in lead 104.

The diameter of typical percutaneous leads is approximately 0.05 inch. This diameter is based upon the diameter of the needle utilized in the surgical procedure to deploy the lead and upon other clinical anatomical requirements. The length of such percutaneous SCS leads is based upon other clinical anatomical requirements. The length of such percutaneous SCS leads is typically 28 centimeters; however, other lengths are utilized to meet particular needs of specific patients and to accommodate special implant locations.

Lead length is an important factor in determining the suitability of using the lead in an MRI environment. For example, the greater length of the lead, the larger the effective loop area that is impacted by the electromagnetic field (i.e. the longer the lead, the larger the antenna). Furthermore, depending on the lead length, there can be standing wave effects that create areas of high current along the lead body. This can be problematic if the areas of high current are near the distal electrodes.

Compared to the helically wound lead, the cable lead has a smaller DC resistance because the length of the straight filer is less than that of a coiled filer and the impedance at high frequency is reduced because the inductance has been significantly reduced. It has been determined that the newer cabled filer designs tend to be more problematic in an MRI environment than do the wound helix filer designs. It should be noted that straight filers for cable leads sometimes comprise braided stranded wire that includes a number of smaller strands woven to make up each filer. This being the case, the number of strands could be varied to alter the impedance.

It has been discovered that high lead impedances at MRI operational frequencies can reduce the heating of an electrode during an MRI procedure. The high impedance acts as a choke for current flowing through the lead and increases real losses along the length of the lead. These two mechanisms reduce electrode heating. As previously alluded to, leads have been intentionally designed with low impedance to enhance system stimulation efficiency. Thus, the simplest way to increase the impedance of a lead is to increase its DC resistance.

For example, the resistance R of a lead filer is governed by the equation:

$$R = \frac{L}{\sigma a} \qquad \text{Equation (1)}$$

where R is the resistance, L is the length of the filer, $\sigma$ is the conductivity, and a is the cross-sectional area. Decreasing the conductivity and/or the cross-sectional area of the filer will increase resistance proportionally. One typical lead utilizes a chromium-cobalt (non-cored MP35N) filer having a conductivity of $1.1 \times 10^6$ mhos/meter, a diameter of approximately 0.005 inch, and a length of approximately 100 centimeters. Using Equation (1), the resistance R of the lead is approximately twenty ohms. If the diameter were reduced to 0.002 inch, R could be increased to approximately 710 ohms (or approximately 126 ohms for a 28 centimeter lead).

Figure 16:
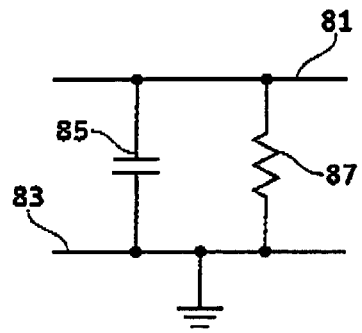
FIGS. 16-19 are schematic diagrams of potential lossy lead configurations.
Figure 17:
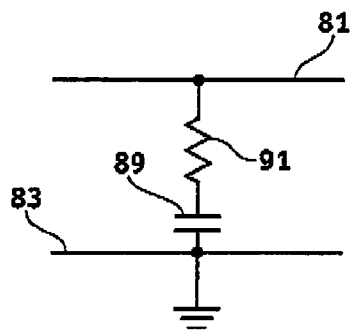
Figure 18:
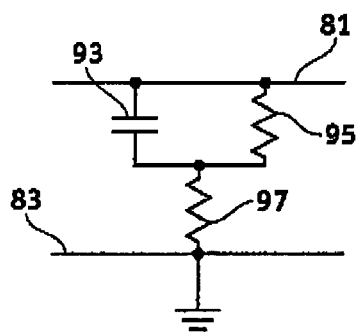
Figure 19:
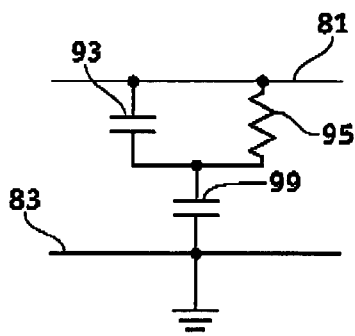

Described below in connection with FIG. 16 is a lead wherein the lead body or lead jacket is configured to shunt induced RF energy from the filers to the patient's body along the length of the lead (or at least a portion thereof). That is, the lead body or lead jacket itself acts as a distributed shunt from the conductive lead filers to the patient's body during an MRI scan. This may be accomplished by (1) providing a shunt conductance (i.e. a DC path) between a filer and a patient's body creating a current path regardless of frequency; (2) a shunt capacitance (i.e. an AC current path) that allows current to flow at high frequency (i.e. MRI frequencies and not stimulation frequencies); or (3) a combination of a shunt conductance and a shunt capacitance. Each of these three mechanisms will create a lossy lead. For example, FIGS. 16-19 are schematic diagrams illustrating how the lossy jacket may be configured. If a filer is represented by conductor 81 and a patient's body is represented by a grounded conductor 83, FIG. 16 illustrates a capacitive shunt 85 in parallel with a conductive shunt 87. In FIG. 17, the shunt is comprised of the series combination of resistor 89 and capacitor 91. In FIG. 18, the shunt comprises the parallel combination of capacitor 93 and resistor 95 in series with resistor 97, and in FIG. 19, series resistor 97 is replaced by a series capacitor 99. This approach is equally applicable to the extension 100 described above in connection with FIGS. 14 and 15. Thus, the term "lead" as hereinafter used is intended to include such lead extensions. In the case of a DC current path, it is recommended that the resistance of the DC path be at least ten times that of the stimulation path.

FIG. 20 is a longitudinal view of a medical lead illustrating a partially exploded portion of lead jacket 120. FIG. 21 is a cross-sectional view of the lead shown in FIG. 20 taken along line 21-21. The lead shown in FIGS. 20 and 21 is substantially similar to that shown in FIGS. 12 and 13 respectively and therefore like reference numerals denote like elements. Straight filers 98 shown in FIG. 21 are each provided with protective insulation 121 (e.g. Teflon), and jacket 120 may be made from materials such as silicone, polyether urethane, etc.

In order to produce a lead jacket 120 that acts as a shunt at high frequency along the length thereof, the jacket material may be doped with a dielectric material such as carbon, talc, and minerals such as calcium carbonate, titanium dioxide, aluminum dioxide, sapphire, mica, and silica. Both pyrolitic and vitreous carbon would be suitable. In any case, the dopant should be biocompatible and preferably have a dielectric constant greater than five. Both the type and concentration of dopant is selected to obtain the desired frequency response in accordance with known techniques.

The dopant is represented graphically in FIGS. 20 and 21 as particles 122. These particles form tiny capacitors with each other and with the conductive filers so as to conduct induced RF energy at high frequencies from filers 98 to body tissue or fluids. The doping concentration may be uniform or non-uniform along the length of the lead. For example, only certain portions of the lead might be doped; e.g. the distal end of the lead close to the stimulation electrode so as to create a different characteristic impedance than the rest of the lead. Alternatively, the dopant concentration may vary along the length of the lead. This change in characteristic impedance could create a reflection at high frequencies so as to keep induced RF energy away from the stimulation electrode.

The lead body or jacket may be provided with a plurality of pores 124 shown in FIGS. 22 and 23, which are longitudinal and cross-sectional views, respectively. Pores 124 (produced by means of, for example, laser drilling) permit body fluid to enter the lead and create a larger capacitance between the patient's body and lead filers 98. This larger capacitance at higher frequency would enhance the conduction of induced RF energy from filers 98 to the patient's body. As was the case previously in connection with the doped jacket of FIGS. 20 and 21, pores 124 may be placed anywhere along the length of the lead (e.g. close to the stimulation electrodes) or the pore density may be varied along the length of the lead. If desired, the jacket may be doped in addition to being provided with pores 124.

Figure 26:
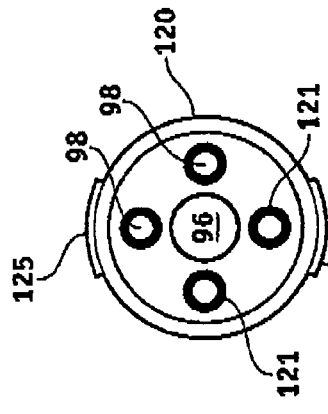
FIGS. 24-30 illustrate still further embodiments of the present invention.
Figure 25:
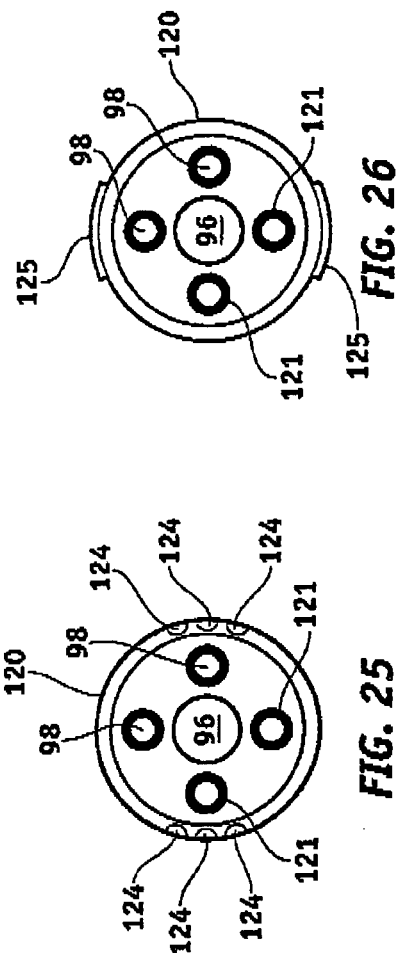
Figure 24:
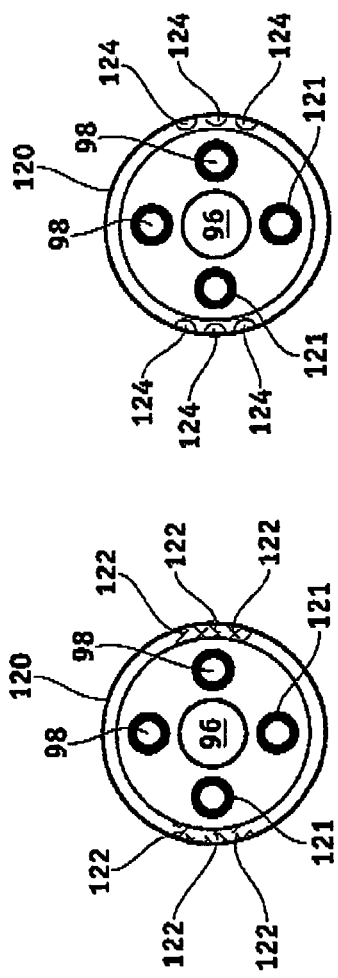
Figure 27:
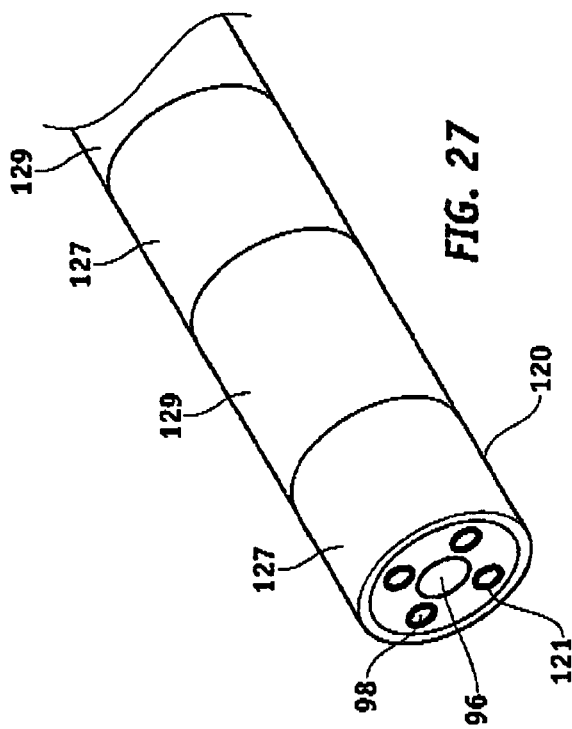

The dopant and/or pores may be concentrated in a longitudinal path limited to one or more selected circumferential sectors as is shown in FIGS. 24 and 25, respectively, or the concentration of dopant may be varied circumferentially. Thus, the concentrations of dopant and pores can vary both longitudinally and circumferentially. If desired, one or more conductive strips 125 may be disposed longitudinally along the length of the lead (or a portion thereof) as is shown in FIG. 26. Still alternatively, the jacket material may be varied along the length of the lead to provide different lossy conduction at different locations. For example, in FIG. 27, sheath 120 may be comprised of alternating sections 127 and 129 of dielectric (e.g. urethane) and conductive sections (e.g. titanium, platinum, stainless steel, conductive polymers, chromium-cobalt alloys, etc.), respectively.

Figure 28:
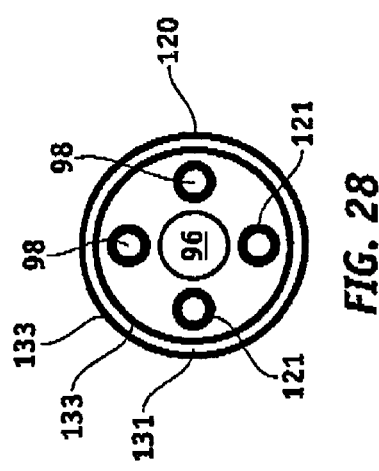
Figure 29:
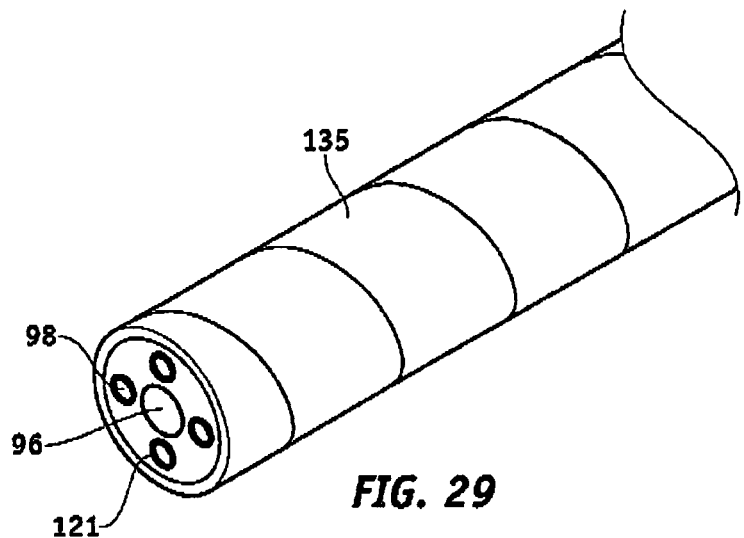
Figure 30:
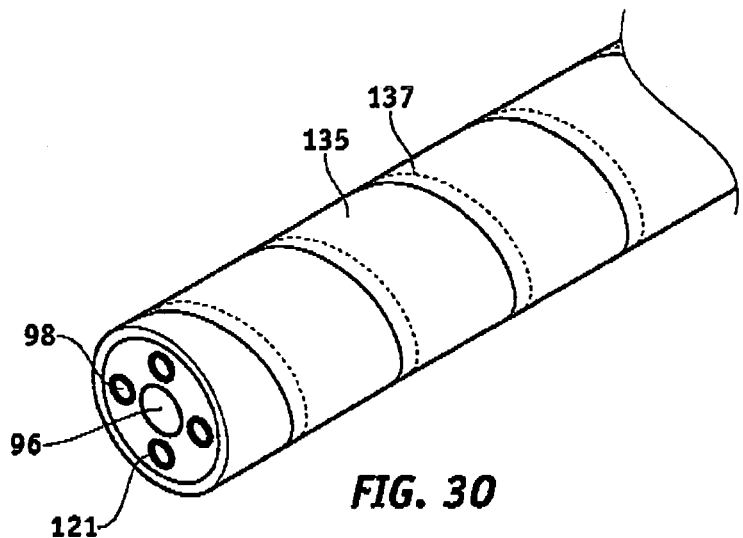

In FIG. 28, a multi-layered jacket of the type shown in FIG. 28 is shown including, for example, alternating layers 131 and 133 of dielectric and conductive material, respectively; e.g. alternating layers of Teflon™ impregnated to be conductive or non-conductive. The alternating layers may be produced by, for example, co-extrusion, dispersion, coating, vapor deposition or atomized coating in accordance with known techniques; or alternatively, the lead jacket could be wrapped with alternating conductive and non-conductive layers to create a shunt capacitance. This could be done using two conductive layers (e.g. doped Teflon™ or PTFE) and one dielectric layer (e.g. PTFE doped with a dielectric material as is shown in FIGS. 29 and 30. Layers could be, for example, extruded or wrapped. Preferably, the two conductive layers are wrapped and the intermediate non-conductive layer is extruded. In FIG. 29, the layers 135 are wrapped in an edge-abutting manner, whereas in FIG. 30, the layers are wrapped in an overlapping manner as indicated by dotted line 137. These techniques are equally applicable to the filer itself, insuring that there is no conduction from filer-to-filer and creating a capacitance around the filer that conducts at high frequency. For example, FIG. 39 illustrates a medical lead comprised of a plurality of filers jacketed as described above and bundled as, for example, by adhering or otherwise securing the jacketed filers.

Figure 31:
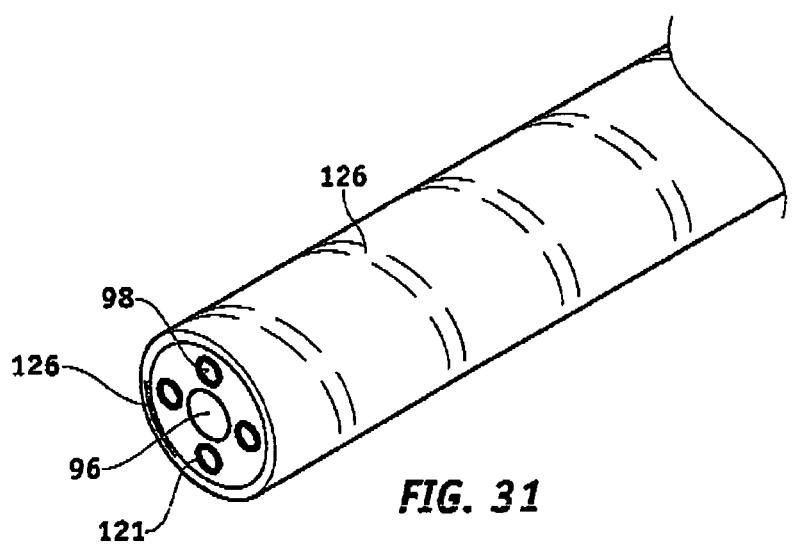

FIGS. 31-36 illustrate a lead incorporating a helical coil of wire that forms a continuous first plate of a capacitor, the second plate being each of the conductive filers 98. This increases the capacitance to the patient's body to shunt induced RF energy to the patient's body at MRI frequencies. Helical coil 126 may take the form of a flat ribbon and may be imbedded in lead jacket 120 as is shown in FIGS. 31 and 32 which are isometric and cross-sectional views respectively. It is known that $$C = \frac{\varepsilon A}{d} \qquad \text{Equation (2)}$$

where C is the capacitance, A is the area of the capacitor plates, d is the distance between the plates and ε is the dielectric constant of the material between them. It can be seen that the capacitance increases with area. Thus, the use of a flat ribbon coil will increase the capacitance. It should also be apparent that the smaller the distance between coil 126 and filers 98, the greater the capacitance between them. Thus, the lead may be constructed so as to place filers 98 closer to jacket 120. Additionally, the capacitance will increase if the jacket is made of a material having a higher dielectric constant.

If desired, jacket 120 may be provided with a plurality of pores 124 to expose coil 126 to body tissue. In addition, coil 126 may be placed on the inner surface of jacket 120 as is shown in FIG. 34 in order to reduce the distance between coil 126 and filers 98. Jacket 120 may be doped with a conductive material or provided with pores in order to increase the capacitance as described above. Alternatively, coil 126 may be positioned on or imbedded within an outer surface of jacket 120 as is shown in FIGS. 35 and 36 which are isometric and cross-sectional views, respectively.

FIG. 37 is a cross-sectional view of a medical lead wherein the region between the insulated filers and the interior surface of jacket 120 is filled with a material 130 (preferably having a dielectric constant greater than three) that creates a capacitance with conductive filers 98. There are a number of biocompatible conductive materials that could be used to backfill the lead; e.g. a saline, conductive gel, gold-plated microspheres, etc. If desired, the conductive gel could fill only selected portions along the length of the lead. Alternatively or additionally, the entire lead jacket 120 may be made of a flexible biocompatible conductive material.

In order to maximize the losses along the lead body, the entire lead jacket could be removed (i.e. the lead is manufactured without a lead jacket) as shown in FIG. 38, or no lead jacket is placed around selected portions of the lead as is shown at 132. The individual filers are separated from each other and from the patient's body tissue or fluids by the insulation 121 on each of the conductive filers. Certain areas of the lead that are most prone to damage could be provided with a lead jacket while other portions of the lead are jacket-free. Optionally, a lead may be provided with a jacket that could be retracted or removed after the lead has been implanted. This provides for good handling and steerability while maximizing its lossy characteristics along the length of the lead.

Flexibility, handling, and extensibility are important features of an implantable therapy lead to accommodate patient movement as previously mentioned. To this end, lead jacket 120 of the lead shown in FIGS. 20 and 21 may comprise a loaded or doped extensible material such as polytetrafluoroethylene (PTFE) that is longitudinally compressed, ensuring that the lead is lossy as previously described while still ensuring that the lead meets the requirements of flexibility, handling, and extensibility.

Figure 40:
FIG. 40 illustrates a strip of longitudinally compressible material, (e.g. PTFE)
Figure 41:
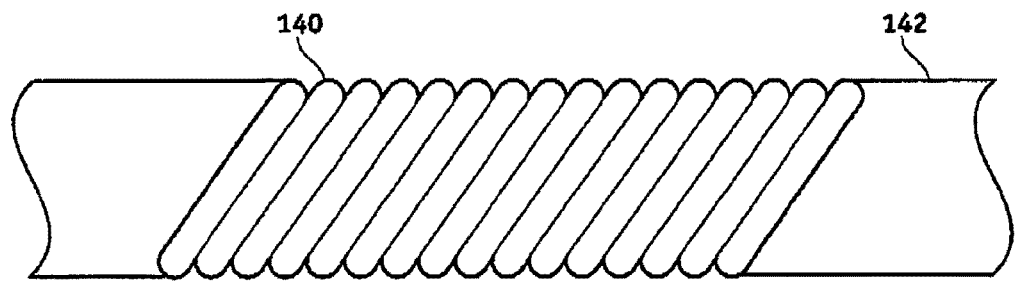
FIG. 41 illustrates and extendable lead utilizing a wrapped PTFE strip.

A strip of PTFE material 140 (shown in FIG. 40) may be doped with a conductive polymer or other conductive material (e.g. metal) and wrapped around a lead assembly 142 to create a lossy outer jacket and/or around each filer to make each filer lossy as is shown in FIG. 41. If desired, a longitudinally compressed, conductively doped PTFE could be alternated with a longitudinally compressed non-conductive PTFE to ensure that there is no conductive path between filers.

In order to provide an extensible lead, the lead filers must also be extensible. This may be accomplished by utilizing coiled filers, preferably of small diameter (e.g. no greater than 0.004 inch), and high impedance to dissipate heat during an MRI scan. A coiled filer may be positioned in the outer jacket with its longitudinal axis substantially parallel to a longitudinal axis of the jacket to provide electromagnetic shielding during MRI and to prevent lead crushing and/or kinking. Helically wound filers result in longer filer length, thus increasing DC resistance.

Figure 42:
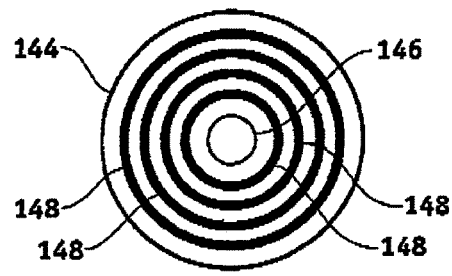
FIG. 42 illustrates a further embodiment of the present invention utilizing concentric coiled filers.

FIG. 42 illustrates an extensible lead having a lead body 144 and stylet lumens 146 and utilizing a plurality (e.g. four) wound filers 148. The filers may be concentric, and each wound filer has a longitudinal axis substantially parallel to that of the jacket. Such filers may be wound in the same or in opposite directions. Any insulation (121 in FIG. 21) around the filers and stylet lumens may be made of a longitudinally compressed material such as PTFE.

Positioning a coiled filer in the lead's outer jacket region will act as an electromagnetic shield in an MRI environment and protect the lead from kinking or crushing. This outer filer may be provided with or without conductive doping in the PTFE. In addition, the longitudinally compressed PTFE may be provided over or wrapped on top of this outer jacket filer.

Figure 43:
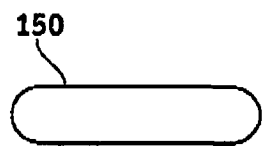
FIG. 43 is a cross-sectional view of the substantially flat filer.

The outer jacket filer 150 preferably has a substantially flat cross-section without sharp edges, such as shown in FIG. 43. Such a filer may be produced by flattening a cylindrical wire. A flattened filer of this type also provides greater shielding coverage of the lead during an MRI scan.

Figure 44:
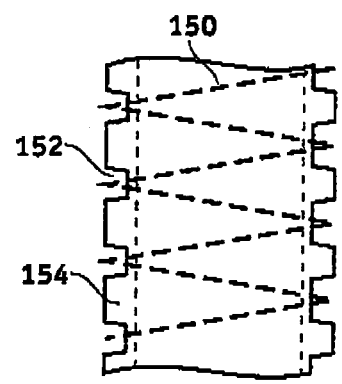
FIG. 44 illustrates an implantable medical lead having a helical channel in the inner layer of an outer lead jacket.
Figure 45:
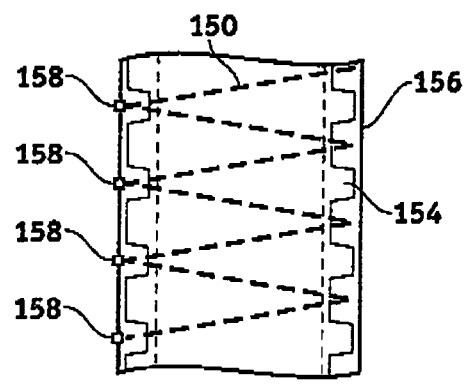
FIG. 45 illustrates the lead shown in FIG. 44 having a secondary outer jacket around the helical channel.

Referring to FIG. 44, filer 150 may be positioned in a helical channel 152 in a layer 154 of the lead's outer jacket. This arrangement permits contact between filer 150 and the patient's body tissue or fluid so as to dissipate energy during an MRI scan. If desired, an outer jacket layer (e.g. insulating layer 156) may be deployed around layer 154 as shown in FIG. 45.

Layer 156 may be thin or be provided with holes 158 therein to permit contact between filer 150 and the surrounding tissue. It may also be doped with a conductive material to place it in electrical contact with the surrounding tissue. Layer 156 may comprise a PTFE doped with conductive material and may be porous to permit contact between filer 150 and body fluids.

While at least one exemplary embodiment has been presented in the foregoing detailed description of the invention, it should be appreciated that a vast number of variations exist. For example, while the invention has been described in connection with neurostimulation systems, the invention is equally applicable to other lead assemblies (e.g. implantable cardiac leads) that may be adversely impacted in high frequency environments such as is encountered during an MRI scan. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims.

What is claimed is:

1. An implantable medical device, comprising:
   a housing;
   an implantable pulse generator within said housing for generating stimulation pulses; and
   a medical lead extending from said housing and further comprising at least one extensible conductive filer and a porous outer jacket providing an outermost layer of the medical lead, said outer jacket comprising a material that is in a longitudinally compressed state, the at least one extensible conductive filer being positioned in the material of the outer jacket that is in the longitudinally compressed state.

2. An implantable medical device according to claim 1 wherein said at least one filer is coiled.

3. An implantable medical device according to claim 1 wherein said at least one conductive filer is coiled, the coiled filer having a longitudinal axis substantially parallel to a longitudinal axis of said jacket.

4. An implantable medical device according to claim 1 further comprising a plurality of coiled filers each having a longitudinal axis substantially parallel to a longitudinal axis of said jacket.

5. An implantable medical device according to claim 1 wherein said outer jacket has a helical channel therein and further comprising a coiled outer filer that resides within said channel.

6. An implantable medical device, comprising:
   a housing;
   an implantable pulse generator within said housing for generating stimulation pulses; and
   a medical lead extending from said housing and comprising at least one extensible conductive filer and a porous outer jacket providing an outermost layer of the medical lead, said outer jacket comprising a material in a longitudinally compressed state and said outer jacket contacting the filer.

* * * * *